(12) United States Patent
Konishi et al.

(10) Patent No.: US 11,067,590 B2
(45) Date of Patent: Jul. 20, 2021

(54) AUTOMATIC ANALYSIS DEVICE

(71) Applicant: Hitachi High-Technologies Corporation, Tokyo (JP)

(72) Inventors: Rei Konishi, Tokyo (JP); Akihisa Makino, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 0 days.

(21) Appl. No.: 16/612,834

(22) PCT Filed: May 11, 2018

(86) PCT No.: PCT/JP2018/018270
§ 371 (c)(1),
(2) Date: Nov. 12, 2019

(87) PCT Pub. No.: WO2018/230217
PCT Pub. Date: Dec. 20, 2018

(65) Prior Publication Data
US 2020/0200784 A1    Jun. 25, 2020

(30) Foreign Application Priority Data

Jun. 16, 2017 (JP) .............................. JP2017-118240

(51) Int. Cl.
*G01N 35/10* (2006.01)
*G01N 35/00* (2006.01)
(Continued)

(52) U.S. Cl.
CPC ......... *G01N 35/1002* (2013.01); *G01N 33/86* (2013.01); *G01N 35/0092* (2013.01);
(Continued)

(58) Field of Classification Search
None
See application file for complete search history.

(56) References Cited

U.S. PATENT DOCUMENTS

| 3,690,833 A | 9/1972 | Ferrari |
| 6,691,748 B1 | 2/2004 | Tajima |
| (Continued) | | |

FOREIGN PATENT DOCUMENTS

| CN | 103439523 A | 12/2013 |
| JP | 2001-194372 A | 7/2001 |
| (Continued) | | |

OTHER PUBLICATIONS

International Search Report of PCT/JP2018/018270 dated Aug. 7, 2018.
(Continued)

*Primary Examiner* — Neil N Turk
(74) *Attorney, Agent, or Firm* — Mattingly & Malur, PC

(57) ABSTRACT

A sample dispensing mechanism configured to dispense a sample and a reagent to the reaction vessel at a first dispensing position and the reaction cell positioned at a second dispensing position; a second reagent vessel disposed on a track of the sample dispensing mechanism; and a control unit configured to control the sample dispensing mechanism, in which the control unit is configured to, based on information on presence or absence of incubation of an analysis item, control the sample dispensing mechanism to dispense a sample and a reagent to the reaction vessel positioned at the first dispensing position in a case where the incubation is not required by the analysis item, and control the sample dispensing mechanism to dispense a sample to the reaction cell positioned at the second dispensing position in a case where the incubation is required by the analysis item.

9 Claims, 5 Drawing Sheets

(51) Int. Cl.
*G01N 33/86* (2006.01)
*G01N 35/02* (2006.01)
*G01N 21/47* (2006.01)

(52) U.S. Cl.
CPC ....... *G01N 35/025* (2013.01); *G01N 35/1004* (2013.01); *G01N 35/1009* (2013.01); *G01N 35/1011* (2013.01); *G01N 21/47* (2013.01)

(56) References Cited

U.S. PATENT DOCUMENTS

| | | | |
|---|---|---|---|
| 2003/0021728 A1* | 1/2003 | Sharpe, Jr. | ....... G01N 35/00584 422/67 |
| 2009/0148345 A1 | 6/2009 | Hamazumi et al. | |
| 2015/0104351 A1 | 4/2015 | Makino et al. | |
| 2015/0362516 A1 | 12/2015 | Meyer et al. | |

FOREIGN PATENT DOCUMENTS

| | | | |
|---|---|---|---|
| JP | 2002-131321 A | 5/2002 |
| JP | 2009-139245 A | 6/2009 |
| JP | 2016-001176 A | 1/2016 |
| WO | 2013/187210 A1 | 12/2013 |

OTHER PUBLICATIONS

Extended European Search Report received in corresponding European Application No. 18817266.2 dated Feb. 16, 2021.

* cited by examiner

[FIG. 1]
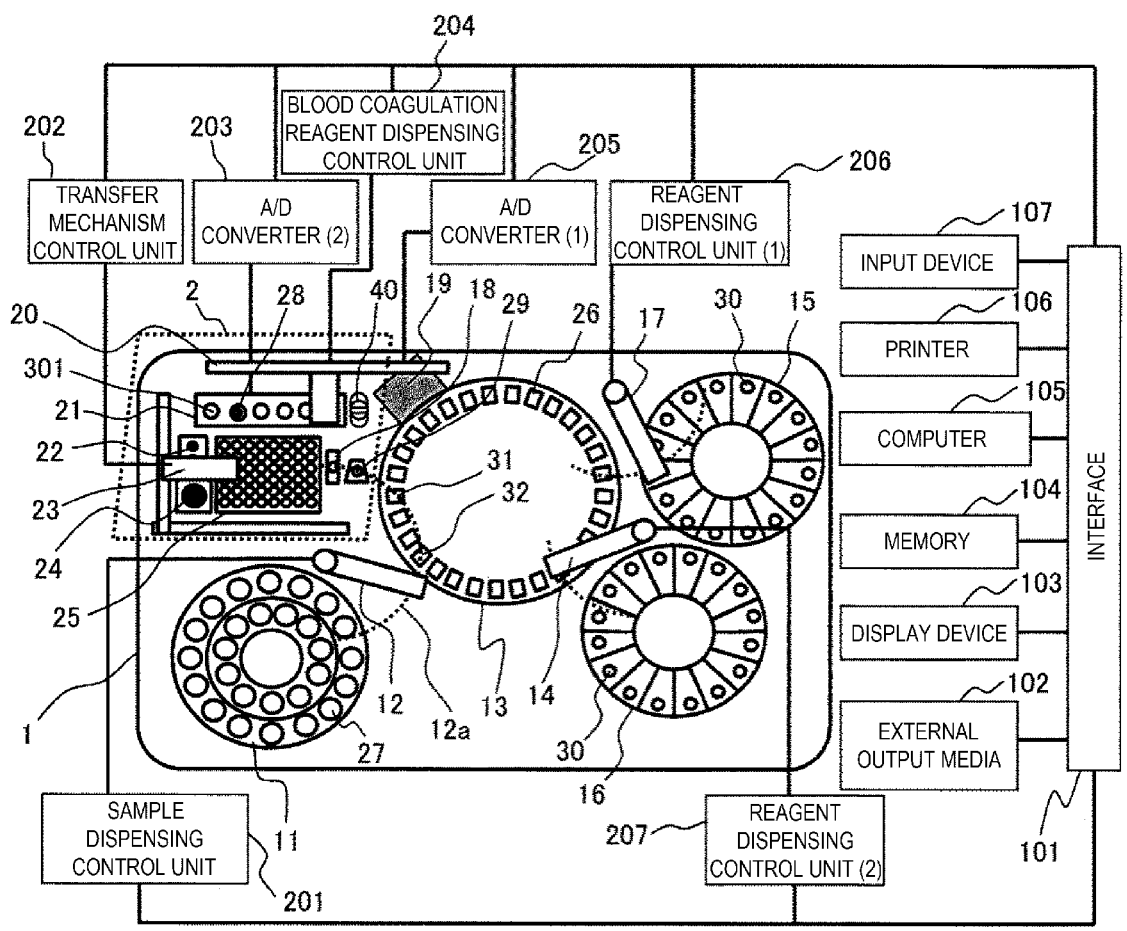

[FIG. 2]
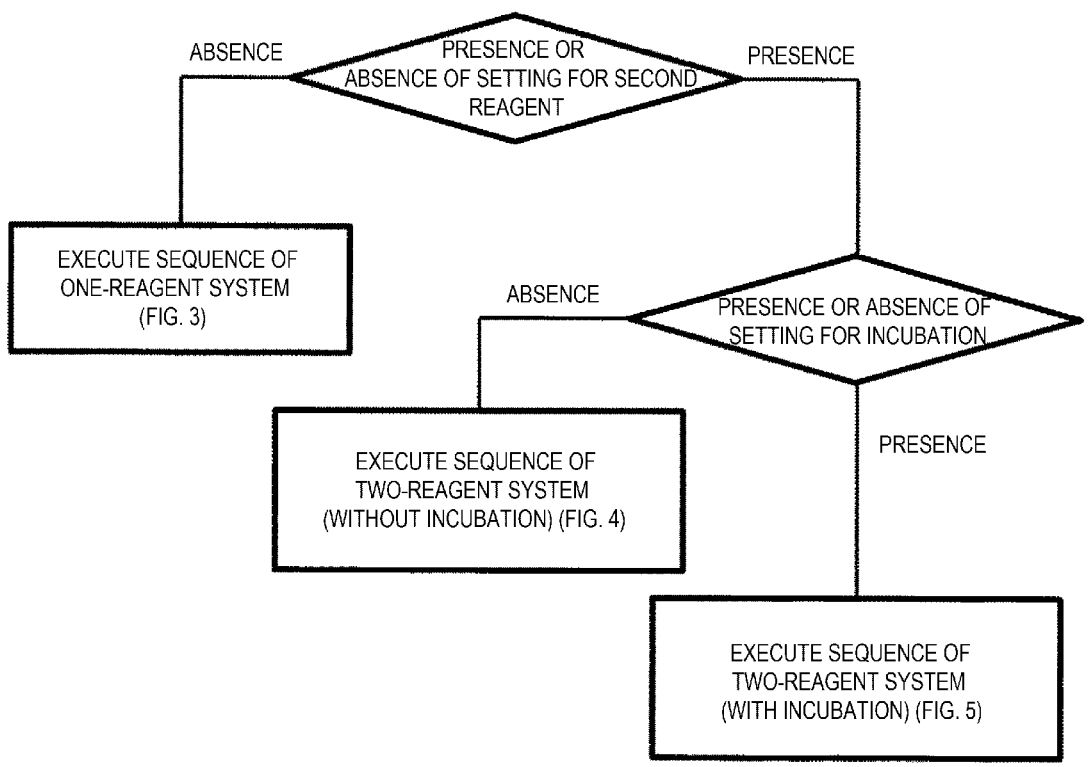

[FIG. 3]
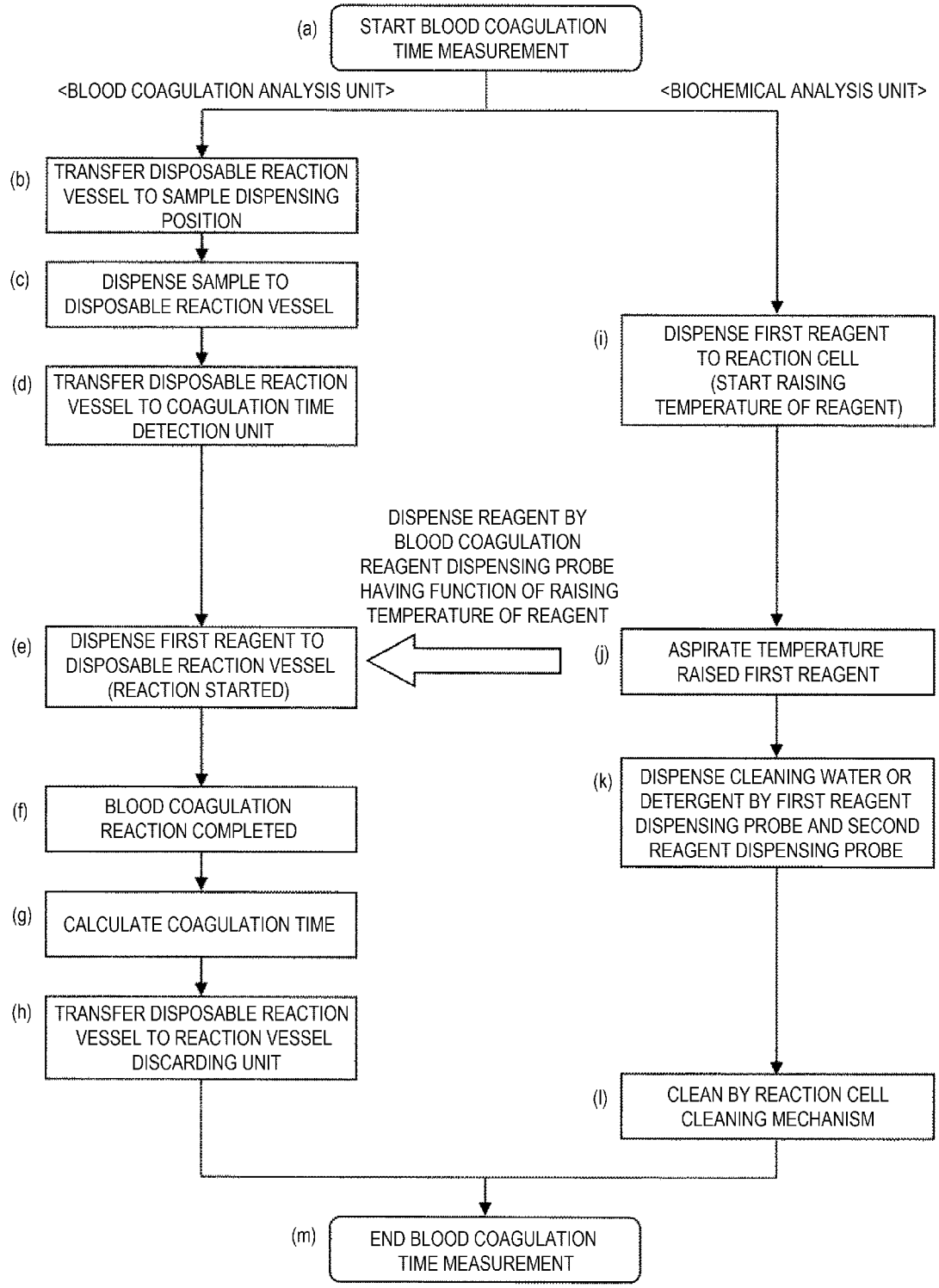

[FIG. 4]
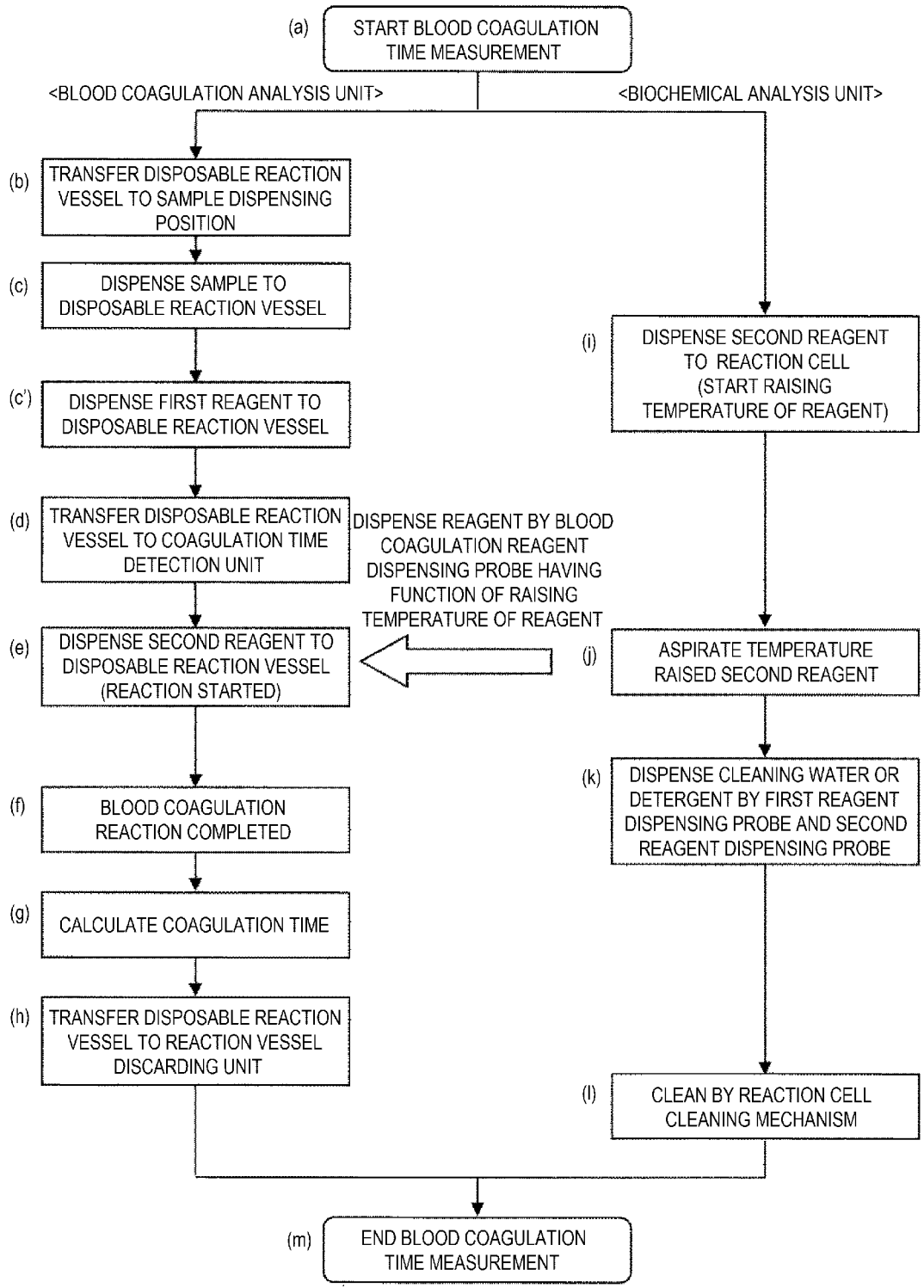

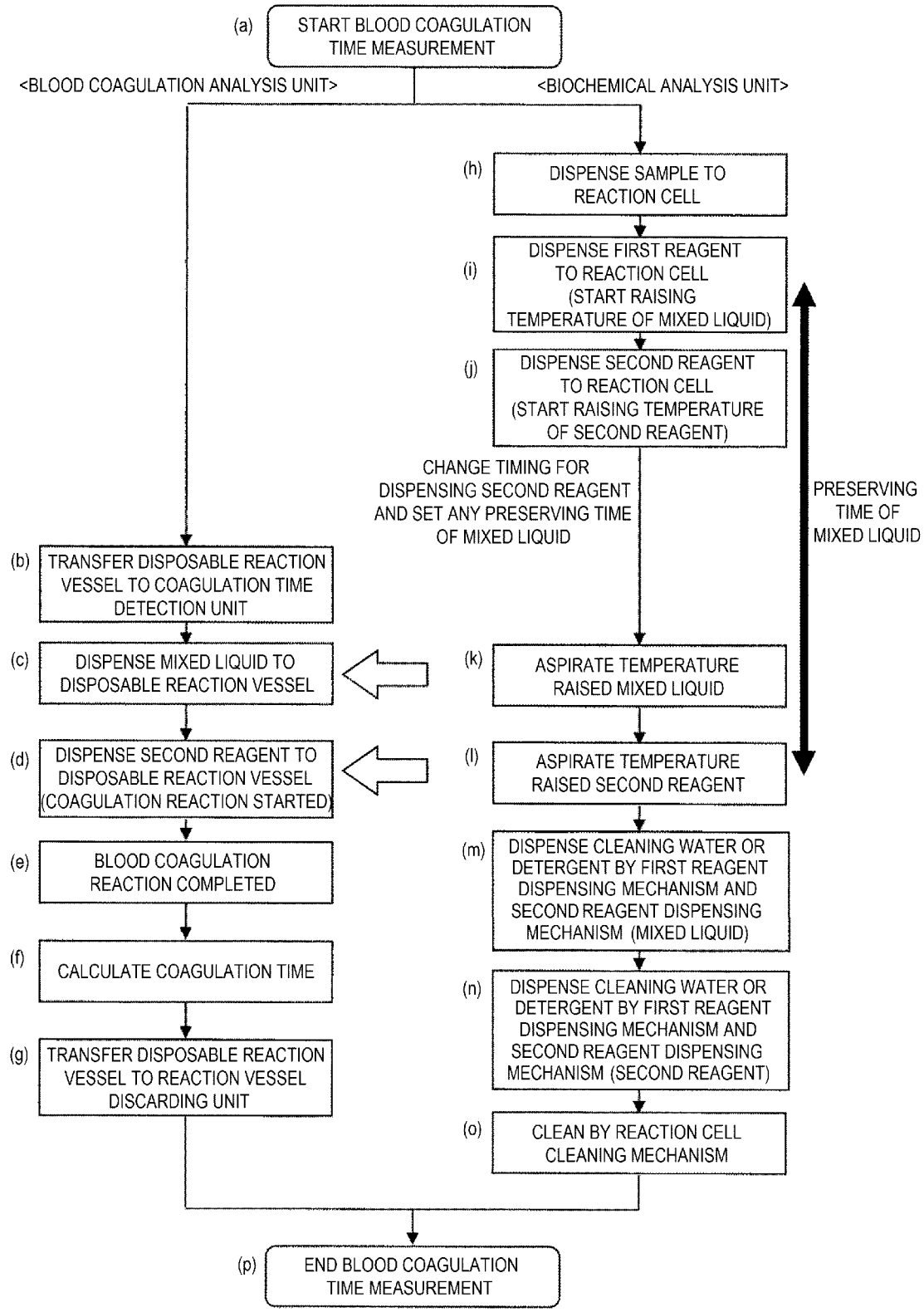

AUTOMATIC ANALYSIS DEVICE

TECHNICAL FIELD

The present invention relates to an automatic analysis device that automatically analyzes a component contained in a biological sample such as blood.

BACKGROUND ART

As an analysis device that analyzes an amount of components contained in a sample, there is known an automatic analysis device that measures an amount of transmitted light or scattered light of a single wavelength or a plurality of wavelengths obtained by irradiating a reaction liquid in which a sample and a reagent are mixed with light from a light source, so as to calculate a component amount based on a relationship between a light amount and a concentration.

The automatic analysis device includes a biochemical analysis device that performs quantitative and qualitative analyses of target components in a biological sample in the fields of a biochemical inspection and a blood inspection, a blood coagulation analysis device that measures coagulation ability of blood which is a sample, and the like.

In an automatic analysis device described in Patent Literature 1 in which a biochemical analysis unit and a blood coagulation analysis unit are integrated, there is known a technique in which a sample dispensing probe is configured to dispense a sample to a reaction cell (for biochemical analysis) or a reaction vessel (for blood coagulation analysis) according to an analysis item measured by a blood coagulation time measurement unit. As described above, when the analysis item is a one-reagent system item, a sample is dispensed to the reaction vessel (for blood coagulation analysis), and a reaction disk is rotated without the sample being dispensed into the reaction cell (for biochemical analysis) to produce an empty reaction cell, and a reagent for measuring blood coagulation time is dispensed to the empty reaction cell by using a first reagent dispensing mechanism. When the analysis item is a two-reagent system item, a sample is dispensed into the reaction cell (for biochemical analysis), and the first reagent dispensing mechanism dispenses a first reagent or a diluted solution to the reaction cell; after the mixed liquid thereof is held for a predetermined time in the reaction cell, a second reagent dispensing mechanism having a reagent temperature raising function dispenses the mixed liquid into the reaction vessel. Further, a second reaction cell (for biochemical analysis) that stores a reagent (second reagent) for initiating a blood coagulation reaction and to be dispensed to the mixed liquid dispensed in the reaction vessel is provided separately from a reaction cell that stores the mixed liquid. A sample dispensing control unit controls a sample dispensing mechanism so that the second reaction cell is an empty reaction cell by rotating the reaction disk without the sample being dispensed into the second reaction cell. The reagent (second reagent) for initiating blood coagulation is dispensed to the second reaction cell which is an empty reaction cell.

PRIOR ART LITERATURE

Patent Literature

PTL 1: WO2013/187210

SUMMARY OF INVENTION

Technical Problem

As described above, in a two-reagent system blood coagulation analysis item for a sample dilution, the sample and the first reagent (diluted solution or the like) are mixed in the reaction cell (for biochemical analysis) and a second reagent is dispensed to the second reaction cell (for biochemical analysis), and therefore, two reaction cells (for biochemical analysis) are required, leading to a decrease in the processing capacity of biochemical analysis.

Solution to Problem

One aspect of the invention for solving the above problems provides an automatic analysis device including: a reaction cell in which a sample and a reagent are mixed and reacted; a first reagent dispensing mechanism configured to dispense a reagent to the reaction cell; a first reagent vessel disposed on a track of the first reagent dispensing mechanism; a reaction vessel in which a sample and a reagent are mixed and reacted; a second reagent dispensing mechanism configured to aspirate a reagent from the reaction cell and dispenses the reagent to the reaction vessel; a sample dispensing mechanism configured to dispense a sample and a reagent to the reaction vessel at a first dispensing position and the reaction cell positioned at a second dispensing position; a second reagent vessel disposed on a track of the sample dispensing mechanism; and a control unit configured to control the sample dispensing mechanism, in which the control unit is configured to, based on information on presence or absence of incubation of an analysis item, control the sample dispensing mechanism to dispense a sample and a reagent to the reaction vessel positioned at the first dispensing position in a case where the incubation is not required by the analysis item, and control the sample dispensing mechanism to dispense a sample to the reaction cell positioned at the second dispensing position in a case where the incubation is required by the analysis item.

Advantageous Effect

According to the above-described embodiment, for the analysis item of a two-reagent system (without incubation) that does not require incubation, the reaction cell (for biochemical analysis) 26 in which the sample and the first reagent (diluted solution or the like) are mixed is not used, so that a decrease in the processing capacity of biochemical analysis can be prevented. Further, since the first reagent can be dispensed at timing of dispensing the diluted solution in the related art, a waiting time can be shortened, which contributes to improvement in the processing capacity of blood coagulation time analysis.

On the other hand, for the analysis item of a two-reagent system that require incubation, the reaction cell (for biochemical analysis) 26 is used, so that there is no need to provide an incubation time at a reaction port 301 of a blood coagulation time detection unit 21, and therefore, the reaction port 301 can be used effectively, which contributes to the improvement in the processing capacity of blood coagulation time analysis.

BRIEF DESCRIPTION OF DRAWINGS

FIG. 1 is a diagram illustrating a basic configuration of an automatic analysis device according to a first embodiment.

FIG. 2 is a flow chart illustrating a measurement sequence determination process of an analysis item according to the first embodiment.

FIG. 3 is a flow chart illustrating a measurement sequence of a one-reagent system according to the first embodiment.

FIG. 4 is a flow chart illustrating a measurement sequence of a two-reagent system (without incubation) according to the first embodiment.

FIG. 5 is a flow chart illustrating a measurement sequence of a two-reagent system (with incubation) according to the first embodiment.

DESCRIPTION OF EMBODIMENTS

In the present specification, an item using only a first reagent for analysis is described as a one-reagent system, and an item using a first reagent and a second reagent is described as a two-reagent system.

First Embodiment

<Basic Configuration of Device>

FIG. 1 is a diagram illustrating a basic configuration of an automatic analysis device according to the embodiment. Here, as an aspect of the automatic analysis device, an example of a complex automatic analysis device including a turntable type biochemical analysis unit and a blood coagulation time analysis unit will be described.

As shown in the figure, an automatic analysis device 1 includes a reaction disk 13, a sample disk 11, a first reagent disk 15, a second reagent disk 16, a blood coagulation time analysis unit 2, and a photometer 19 which are disposed on a housing thereof.

The reaction disk 13 is a disk-shaped unit that is rotatable in a clockwise direction and a counterclockwise direction, and a plurality of reaction cells (for biochemical analysis) 26 can be disposed on a circumference of the reaction disk 13.

The sample disk 11 is a disk-shaped unit that is rotatable in a clockwise direction and a counterclockwise direction, and a plurality of sample vessels 27 that store samples such as a standard sample and a test sample can be disposed on a circumference of the sample disk 11.

The first reagent disk 15 and the second reagent disk 16 are disk-shaped units that are rotatable in a clockwise direction and a counterclockwise direction, and a plurality of reagent vessels 30 that store a reagent containing a component that reacts with a component of respective inspection items contained in a sample can be disposed on circumferences of the first reagent disk 15 and the second reagent disk 16. Although not shown in the figure, the first reagent disk 15 and the second reagent disk 16 may be provided with a cold storage mechanism or the like, so that the reagent in the disposed reagent vessels 30 can be kept cold. A configuration in which both first reagent and second reagent used in a two-reagent system are disposed on the first reagent disk 15, a configuration in which both first reagent and second reagent are disposed on the second reagent disk 16, a configuration in which the first reagent or the second reagent is disposed in each of the first reagent disk 15 and the second reagent disk 16, and the like are considered, whether the reagent is disposed on the first reagent disk 15 or the second reagent disk 16 may be freely set by an operator.

A sample dispensing probe 12 is disposed between the sample disk 11 and the reaction disk 13 so as to perform a sample and reagent aspiration and a dispensing operation in the sample vessels 27 on the sample disk 11, the reaction cell 26 on the reaction disk 13, and a reaction vessel (for blood coagulation analysis) 28 and a reagent vessel (for blood coagulation analysis) 29 at a first dispensing position 18 of the blood coagulation time analysis unit 2 by a rotational operation of the sample dispensing probe 12. Here, the reagent in the disposed reagent vessel (for blood coagulation analysis) 29 can be cooled by providing the cold storage mechanism or the like at an installation location of the reagent vessel (for blood coagulation analysis) 29. Further, a sample dispensing probe cleaning tank (not shown) is disposed on a track 12a of the sample dispensing probe 12, and the probe can be cleaned. Although a broken line is shown as the track 12a of the sample dispensing probe 12 on the drawing in FIG. 1, the broken line is a part of the track 12a of the sample dispensing probe 12, and not only the broken line but also a rotational track can be drawn.

Similarly, a first reagent dispensing probe 17 is disposed between the first reagent disk 15 and the reaction disk 13, and a second reagent dispensing probe 14 is disposed between the second reagent disk 16 and the reaction disk 13 so as to perform a dispensing operation such as aspiration and dispensing in the reaction cell 26 on the reaction disk 13 and the reagent vessels on the first reagent disk 15 and the second reagent disk 16 by a rotational operation, separately.

The blood coagulation time analysis unit 2 mainly includes a blood coagulation time detection unit 21, a blood coagulation reagent dispensing probe 20, a reaction vessel supply unit 25, a first dispensing position 18, a reaction vessel transfer mechanism 23, a reaction vessel discarding port 24, an optical jig magazine 22, and a blood coagulation reagent dispensing mechanism cleaning tank 40. Here, the blood coagulation time detection unit 21 includes a reaction vessel holding unit (not shown) that can holds the reaction vessels (for blood coagulation analysis) 28, a light source that irradiates the held reaction vessels (for blood coagulation analysis) 28 with light, and a plurality of reaction ports 301 that include a light source for detecting the emitted light. Here, a disposable reaction vessel is used as the reaction vessel (for blood coagulation analysis) 28, and contamination between samples is prevented. Further, since blood clot is solidified by fibrin in the reaction vessel when a blood coagulation time measurement is contained as an analysis item for the sample, it is desirable to set the reaction vessels (for blood coagulation analysis) 28 as the disposable reaction vessel.

Next, a control system and a signal processing system according to the automatic analysis device 1 will be briefly described. A computer 105 is connected to a sample dispensing control unit 201, a reagent dispensing control unit (1) 206, a reagent dispensing control unit (2) 207, a blood coagulation reagent dispensing control unit 204, an A/D converter (1) 205, an A/D converter (2) 203, and a transfer mechanism control unit 202 via an interface 101, and transmits a command to each control unit.

The sample dispensing control unit 201 controls a dispensing operation of a sample by the sample dispensing probe 12 based on a command received from the computer 105.

The reagent dispensing control unit (1) 206 and the reagent dispensing control unit (2) 207 control a dispensing operation of a reagent by the first reagent dispensing probe 17 and the second reagent dispensing probe 14 based on a command received from the computer 105.

The transfer mechanism control unit 202 controls a transfer operation of the reaction vessel (for blood coagulation analysis) 28 among the reaction vessel supply unit 25, the first dispensing position 18, the reaction port 301 of the blood coagulation time detection unit 21, and the reaction vessel discarding port 24 by the reaction vessel transfer mechanism 23 based on a command received from the computer 105.

The blood coagulation reagent dispensing control unit 204 dispenses a reagent for blood coagulation by the blood coagulation reagent dispensing probe 20 to the reaction vessel (for blood coagulation analysis) 28 that stores the sample dispensed by the sample dispensing probe 12 and to be transferred to the reaction port 301 based on a command received from the computer 105. Alternatively, a pretreatment liquid, which is a mixed liquid of the sample and the first reagent for blood coagulation analysis mixed in the reaction cell (for biochemical analysis) 26, is dispensed to empty reaction vessels (for blood coagulation analysis) 28 by the blood coagulation reagent dispensing probe 20. In this case, the second reagent for blood coagulation analysis is then dispensed to the reaction vessels (for blood coagulation analysis) 28 storing the pretreatment liquid.

In the present embodiment, although a plurality of control units control a plurality of mechanisms respectively based on a command from the computer 105, the computer 105 may be configured to directly control the plurality of mechanisms.

A photometric value of transmitted light or scattered light of reaction liquid in the reaction cell (for biochemical analysis) 26 converted into a digital signal by the A/D converter (1) 205 and a photometric value of transmitted light or scattered light of reaction liquid in the reaction vessel (for blood coagulation analysis) 28 converted into a digital signal by the A/D converter (2) 203 are taken into the computer 105.

The interface 101 is connected to a printer 106 for printing when a measurement result is output as a report, a memory 104 and an external output medium 102 which are storage devices, an input device 107 such as a keyboard for inputting an operation command, and a display device 103 for displaying a screen. The display device 103 is, for example, a liquid crystal display, a CRT display.

Analysis of a biochemical item by the automatic analysis device 1 is performed in the following procedure. First, an operator requests an inspection item for each sample by using the input device 107 such as a keyboard. In order to analyze the sample for the requested inspection item, the sample dispensing probe 12 dispenses a predetermined amount of sample from the sample vessel 27 to the reaction cell (for biochemical analysis) 26 positioned at a second dispensing position 31 according to analysis parameters.

The reaction cell (for biochemical analysis) 26 to which the sample is dispensed is transferred by a rotation of the reaction disk 13 and stopped at a reagent dispensing position. Pipette nozzles of the first reagent dispensing probe 17 and the second reagent dispensing probe 14 dispense a predetermined amount of reagent solution to the reaction cell (for biochemical analysis) 26 in accordance with the analysis parameters of the corresponding inspection item. As for a dispensing order between the sample and the reagent, the reagent may precede the sample as opposed to the example.

Thereafter, the sample and the reagent are stirred by a stirring mechanism (not shown) and mixed. When the reaction cell (for biochemical analysis) 26 crosses a photometric position, the transmitted light or the scattered light of the reaction liquid is measured by a photometer. The measured transmitted light or scattered light is converted into numerical data proportional to the amount of light by the A/D converter (1) 205, and taken into the computer 105 via the interface 101.

By using the converted numerical value, concentration data is calculated based on a calibration curve measured in advance by an analysis method designated for each inspection item. Component concentration data as an analysis result of each inspection item is output to the printer 106 or a screen of the display device 103.

The reaction cell (for biochemical analysis) 26 in which the sample and the reagent are mixed is transferred by the rotation of reaction disk 13, and at the timing of being positioned at a third dispensing position 32, the sample dispensing probe 12 can aspirate the mixed liquid, and dispense the mixed liquid into another reaction cell (for biochemical analysis) 26 positioned at the second dispensing position 31.

Here, the second dispensing position 31 and the third dispensing position 32 are disposed on intersections of the track 12a of the sample dispensing probe and a rotational track of the reaction cell (for biochemical analysis) 26 disposed on the circumference of the reaction disk 13, respectively.

Before the measurement operation described above is executed, the operator sets various parameters necessary for analysis and registers a reagent and a sample via an operation screen of the display device 103. Further, the operator confirms an analysis result after the measurement by using the operation screen on the display device 103.

Here, an analysis operation of the blood coagulation time item according to the present embodiment will be described with reference to FIGS. 2, 3, 4, and 5. Before the following measurement operation is executed, the operator sets various parameters necessary for analysis, and registers a reagent and a sample in advance via the operation screen of the display device 103. Further, the operator can confirm an analysis result after the measurement by using the operation screen on the display device 103.

First, the operator requests an inspection item for each sample by using the information input device 107 such as a keyboard. Here, a measurement sequence of each sample is determined according to FIG. 2 in accordance with a setting for the inspection item. First, it is confirmed whether a setting for the second reagent is present, and when the setting for the second reagent is absent, a sequence of a one-reagent system is executed. An example of an analysis item of the one-reagent system is prothrombin time (PT). After it is confirmed that the setting for the second reagent is present, it is checked whether a setting for incubation is present. When the setting for incubation is absent, a sequence of a two-reagent system (without incubation) is executed. An example of an analysis item of the two-reagent system (without incubation) includes an amount of fibrinogen (Fbg) and calibration of Fbg and PT. When the setting for incubation is present, a sequence of a two-reagent system (with incubation) is executed. An example of an analysis item for the two-reagent system (with incubation) includes activated partial thromboplastin time (APTT).

First, FIG. 3 illustrates a flow chart for a one-reagent system item. In order to analyze the sample for the requested inspection item, the reaction vessel transfer mechanism 23 transfers the reaction vessel (for blood coagulation analysis) 28 from the reaction vessel supply unit 25 to the first dispensing position 18 (b). The sample dispensing probe 12 dispenses a predetermined amount of sample from the sample vessel 27 to the reaction vessel (for blood coagulation analysis) 28 disposed at the first dispensing position 18 according to analysis parameters (c). At this time, use of the reaction cells is controlled such that an empty reaction cell (for biochemical analysis) 26 to which the sample is not dispensed is generated on the reaction disk 13. The reaction vessel (for blood coagulation analysis) 28 to which the sample is dispensed is transferred from the first dispensing position 18 to the reaction port 301 of the blood coagulation time detection unit 21 by the reaction vessel transfer mechanism 23, and a temperature of the reaction vessel (for blood coagulation analysis) 28 is raised to a predetermined temperature (d).

The first reagent dispensing probe 17 dispenses the first reagent to the empty reaction cell (for biochemical analysis) 26 to which the sample is not dispensed on the reaction disk 13 according to the analysis parameters of the corresponding inspection item. Since a thermostatic chamber (not shown) is provided to the reaction disk 13, the first reagent dispensed to the reaction cell (for biochemical analysis) 26 is heated to 37° C. (i).

Thereafter, the reaction cell (for biochemical analysis) 26 to which the first reagent is dispensed is transferred by the rotation of the reaction disk 13 to a position where the blood coagulation reagent dispensing probe 20 can aspirate. When the reaction cell (for biochemical analysis) 26 to which the first reagent is dispensed is transferred to an intersection of a rotational track of the reaction disk 13 and a track of the blood coagulation reagent dispensing probe 20, the blood coagulation reagent dispensing probe 20 aspirates the reagent dispensed to the reaction cell (for biochemical analysis) 26 (j). The blood coagulation reagent dispensing probe 20 has a reagent temperature raising function, and after the temperature is raised to a predetermined temperature by a temperature raising mechanism (not shown), the first reagent is dispensed to the reaction vessel (for blood coagulation analysis) 28 (e). In the blood coagulation reagent dispensing probe 20, the sample and the first reagent are mixed in the reaction vessel (for blood coagulation analysis) 28 by a force when the first reagent is dispensed to the sample stored in the reaction vessel (for blood coagulation analysis) 28 already, and stirring called dispensing stirring is performed.

From a time point when the first reagent is dispensed, photometry of transmitted light or scattered light of light emitted to the reaction vessel (for blood coagulation analysis) 28 is started. Measured transmitted light or measured scattered light is converted into data having a numerical value proportional to the light amount by the A/D converter (2) 203, and is taken into the computer 105 via the interface 101. After the reaction is ended (f), the converted numerical value is used to determine a time required for a blood coagulation reaction (hereinafter, simply referred to as blood coagulation time) (g).

Thereafter, the reaction vessel (for blood coagulation analysis) 28 in which the reaction is ended is transferred to the reaction vessel discarding port 24 by the reaction vessel transfer mechanism 23 and discarded (h). Further, cleaning water or detergent is dispensed by the first reagent dispensing probe 17 or the second reagent dispensing probe 14 to the reaction cell (for biochemical analysis) 26 after the first reagent is aspirated (k), and then the reaction cell (for biochemical analysis) 26 is cleaned by a reaction cell cleaning mechanism (not shown) (1).

Next, FIG. 4 illustrates a flow chart for the two-reagent system (without incubation). Here, only a portion different from that in FIG. 3 and the flowchart of the one-reagent system described above will be described. A part described as the first reagent in FIG. 3 and the one-reagent system flow described above is described as the second reagent in the two-reagent system (without incubation).

The sample dispensing probe 12 dispenses a predetermined amount of sample contained in the sample vessel 27 on the sample disk 11 to the reaction vessel (for blood coagulation analysis) 28 disposed at the first dispensing position 18 from the sample vessel 27 in accordance with the analysis parameters (c). Thereafter, the sample dispensing probe 12 is cleaned by a cleaning port (not shown) disposed on the track 12a of the sample dispensing probe 12. After cleaning is completed, the sample dispensing probe 12 dispenses a predetermined amount of the first reagent (diluted solution or the like) to the reaction vessel (for blood coagulation analysis) 28 disposed at the first dispensing position 18 from the reagent vessel (for blood coagulation analysis) 29 according to the analysis parameters and mixes the sample and the first reagent (c'). As for a dispensing order between the sample and the first reagent, the diluted solution may precede the sample as opposed to the example.

Next, FIG. 5 illustrates a flow chart for an item of the two-reagent system (with incubation). The sample is dispensed to the reaction cell (for biochemical analysis) 26 on the reaction disk 13 positioned at the second dispensing position 31 by the sample dispensing probe 12 (h). Thereafter, the reaction cell (for biochemical analysis) 26 to which the sample is dispensed moves to an intersection of a rotational track of the reaction disk 13 and a rotational track of the first reagent dispensing probe 17 by the rotation of the reaction disk 13. The first reagent disposed on the first reagent disk 15 is dispensed to the moved reaction cell 26 by the first reagent dispensing probe 17 (i), and the sample and the reagent are mixed by a stirring mechanism (not shown). Since a thermostatic chamber (not shown) is provided in the reaction disk 13, a temperature of a mixed liquid of the sample and the first reagent which are dispensed to the reaction cell (for biochemical analysis) 26 is raised. Further, the second reagent is dispensed to another reaction cell 26 which is emptied in a predetermined cycle on the reaction disk 13 by the first reagent dispensing probe 17, and a temperature of the second reagent is started to be raised by the thermostatic chamber provided on the reaction disk 13 (j).

The reaction vessel (for blood coagulation analysis) 28 is transferred to the blood coagulation time detection unit 21 of the blood coagulation analysis unit (b), and the mixed liquid of the sample and the first reagent of which the temperature is raised to 37° C. in the reaction cell (for biochemical analysis) 26 on the reaction disk 13 and the second reagent are separately aspirated by the blood coagulation reagent dispensing probe 20 (k to l). Further, after temperatures of the mixed liquid and the second reagent are raised to a predetermined temperature (for example, 40° C.) by a temperature raising mechanism (not shown) disposed on the blood coagulation reagent dispensing probe 20, the mixed liquid and the second reagent are dispensed to the reaction vessels (for blood coagulation analysis) 28 on the blood coagulation time detection unit 21, separately (c). After the second reagent is dispensed, the blood coagulation reaction starts (d). After the reaction is completed (e), a coagulation time is calculated (f), and the reaction vessel (for blood coagulation analysis) 28 is discarded to the reaction vessel discarding port 24 (g). As for a dispensing order between the sample and the first reagent, the reagent may precede the sample as opposed to the example, and in this case, the reagent and the sample can be mixed by a force when the sample is dispensed.

Cleaning water or detergent is dispensed by the first reagent dispensing probe 17 or the second reagent dispensing probe 14 to the reaction cell 26 after the temperature raised mixed liquid of the sample and the first reagent or the temperature raised second reagent is aspirated (m to n). Thereafter, the reaction cell 26 is cleaned by a reaction cell cleaning mechanism (not shown) (o).

The reaction cell (for biochemical analysis) 26 in which the sample and the diluted solution are mixed is transferred by the rotation of the reaction disk 13, and at the timing of being positioned at the third dispensing position 32, the sample dispensing probe 12 can aspirate the mixed liquid, and dispense the mixed liquid into another reaction cell (for biochemical analysis) 26 positioned at the second dispensing position 31. Accordingly, a dilution ratio of the sample can be set freely widely.

According to the embodiment described above, for the analysis item of the two-reagent system (without incubation) that does not require incubation, the reaction cell (for biochemical analysis) 26 for mixing the sample and the diluted solution is not used, so that a reduction in the processing capacity of the biochemical analysis can be prevented. In addition, since the second reagent can be dispensed at the timing of dispensing the diluted solution in the related art (the first reagent in a case of the two-reagent system (without incubation), a waiting time can be shortened, which contributes to improvement in the processing capacity of the blood coagulation time analysis.

On the other hand, for the analysis item of the two-reagent system (with incubation) that requires incubation, the reaction cell (for biochemical analysis) 26 is used, so that there is no need to provide an incubation time in the reaction port 301 of the blood coagulation time detection unit 21, and therefore, the reaction port 301 can be used effectively, which contributes to improvement in the processing capacity of blood coagulation time analysis.

Second Embodiment

In the first embodiment described above, in the sequence for the two-reagent system (without incubation), the configuration is described in which, after the sample dispensing probe 12 dispenses a predetermined amount of samples to the reaction vessel (for blood coagulation analysis) 28, the sample dispensing probe 12 dispenses a predetermined amount of first reagents (diluted solution or the like) to the reaction vessel (for blood coagulation analysis) 28, and the sample and the first reagent are mixed, but in the present embodiment, the sample dispensing probe can continuously aspirate and dispense the sample and the first reagent.

An operation of a sample dispensing probe according to the present embodiment will be described below. After the sample dispensing probe 12 aspirates the sample from the sample vessel 27 in accordance with analysis parameters, an air layer is provided in the probe by aspirating air. Thereafter, an outer wall of the probe is cleaned in a sample dispensing probe cleaning tank, and the sample dispensing probe 12 aspirates a predetermined amount of first reagent (diluted solution or the like) from the reagent vessel (for blood coagulation analysis) 29 in accordance with the analysis parameters. Thereafter, the sample and the first reagent are dispensed to the reaction vessel (for blood coagulation analysis) 28.

After the sample is aspirated, the sample attached to the outer wall of the probe can be cleaned away by cleaning the outer wall of the probe in the sample dispensing probe cleaning tank, and it is possible to prevent the sample from being mixed into the first reagent in the reagent vessel (for blood coagulation analysis) 29.

After the sample is aspirated, the sample held in the probe can be prevented from being mixed into the first reagent in the reagent vessel (for blood coagulation analysis) 29 by providing the air layer in which air is aspirated. Air aspiration timing may be after sample aspiration and before first reagent aspiration, and the same effect can be obtained even after the probe is cleaned.

As for a dispensing order between the sample and the first reagent, the first reagent may precede the sample as opposed to the example. In this case, by aspirating the first reagent first, it is not necessary to aspirate a dummy sample for preventing the sample from being diluted with system water in the probe, and the consumption of the sample can be prevented.

Third Embodiment

In the first embodiment described above, in the measurement sequence for the two-reagent system (without incubation), the configuration is described in which a sample and a first reagent (diluted solution or the like) are mixed by the sample dispensing probe 12, but in the present embodiment, normal plasma can be used instead of the first reagent. In this case, patient plasma which is a sample and normal plasma are mixed by the sample dispensing probe 12, and analysis of a cross mixing test (also referred to as a blood coagulation correction test or an intersection mixing test) can be performed. In addition to being stored in the reagent vessel (for blood coagulation analysis) 29, the normal plasma can also be stored in the sample vessel 27 and placed on the sample disk 11. Note that the present embodiment can also have the same configuration as that of the second embodiment.

Fourth Embodiment

In the first embodiment described above, in the measurement sequence for the two-reagent system (without incubation), the configuration is described in which two liquids including a sample and a first reagent (diluted solution or the like) are mixed by the sample dispensing probe 12, but in the present embodiment, three liquids including coagulation factor deficient plasma in addition to the sample and the first reagent can be dispensed.

In this case, patient plasma which is a sample, coagulation factor deficient plasma, and a diluted solution are mixed by the sample dispensing probe 12 to enable analysis of coagulation factor quantification. At this time, for the coagulation factor deficient plasma, a reagent vessel (for blood coagulation analysis) 29 that stores the coagulation factor deficient plasma may be newly installed on the track 12a of the sample dispensing probe 12 next to the reagent vessel (for blood coagulation analysis) 29 that stores the first reagent (diluted solution or the like), or the coagulation factor deficient plasma may also be stored in the sample vessel 27 and placed on the sample disk 11. Note that the present embodiment can also have the same configuration as that of the second embodiment.

Fifth Embodiment

In the first embodiment described above, the configuration in which a measurement sequence for each sample is determined by a control unit in accordance with a setting for an inspection item, but in the present embodiment, a case where an operator determines the measurement sequence of the inspection item will be described. Even for an inspection item of a two-reagent system (with incubation), a measurement sequence of a two-reagent system (without incubation) can be selected. Accordingly, the reaction port 301 is occupied since incubation needs to be performed at the reaction port 301, but it is effective when the number of analysis requests for biochemical analysis is larger than the number of analysis requests for blood coagulation analysis since the use of the reaction cells (for biochemical analysis) 26 can be reduced. At this time, a second reagent is dispensed by the first reagent dispensing probe 17 to an empty reaction cell (for biochemical analysis) 26 to which the sample is not dispensed. The blood coagulation reagent dispensing probe 20 aspirates the second reagent dispensed to the reaction cell (for biochemical analysis) 26 and the second reagent is held in the blood coagulation reagent dispensing probe 20. By setting any timing of dispensing the second reagent to the reaction vessel (for blood coagulation analysis) 28, an incubation time can be set freely.

The invention is not limited to the embodiments described above, and includes various modifications. For example, the embodiments described above have been described in detail for easy understanding of the invention, the invention is not necessarily limited to those including all the configurations described above. Apart of the configuration of one embodiment can be replaced with the configuration of another embodiment, and the configuration of another embodiment can be added to the configuration of one embodiment. Apart of the configuration of each embodiment may be added, deleted, or replaced with another configuration.

REFERENCE SIGN LIST

1 . . . automatic analysis device
2 . . . blood coagulation time analysis unit
11 . . . sample disk
12 . . . sample dispensing probe
12a . . . track of sample dispensing probe
13 . . . reaction disk
14 . . . second reagent dispensing probe
15 . . . first reagent disk
16 . . . second reagent disk
17 . . . first reagent dispensing probe
18 . . . first dispensing position
19 . . . photometer
20 . . . blood coagulation reagent dispensing probe
21 . . . blood coagulation time detection unit
22 . . . optical jig magazine
23 . . . reaction vessel transfer mechanism
24 . . . reaction vessel discarding port
25 . . . reaction vessel supply unit
26 . . . reaction cell (for biochemical analysis)
27 . . . sample vessel
28 . . . reaction vessel (for blood coagulation analysis)
29 . . . reagent vessel (for blood coagulation analysis)
30 . . . reagent vessel
31 . . . second dispensing position
32 . . . third dispensing position
101 . . . interface
102 . . . external output media
103 . . . display device
104 . . . memory
105 . . . computer
106 . . . printer
107 . . . input device
201 . . . sample dispensing control unit
202 . . . transfer mechanism control unit
203 . . . A/D converter (2)
204 . . . blood coagulation reagent dispensing control unit
205 . . . A/D converter (1)
206 . . . reagent dispensing control unit (1)
207 . . . reagent dispensing control unit (2)
301 . . . reaction port

The invention claimed is:

1. An automatic analysis device comprising: a first reagent disk holding a first reagent;
a second reagent disk holding a second reagent;
a sample disk holding a sample;
a plurality of reaction cells on a reaction disk in which the first reagent is dispensed or the second reagent is dispensed or both a sample and the first reagent are dispensed and mixed, respectively;
a first reagent dispensing mechanism configured to move along a first track to the first reagent disk or the second reagent disk or the reaction disk to dispense the first reagent or the second reagent to a reaction cell on the reaction disk;
a first reagent vessel disposed on the first track of the first reagent dispensing mechanism;
a reaction vessel in which a sample and the first reagent are dispensed and mixed or in which the sample, the first reagent and the second reagent are dispensed and mixed;
a second reagent dispensing mechanism configured to move along a second track to aspirate the first reagent or the second reagent or both the first reagent and the sample from the reaction cell on the reaction disk and dispense the first reagent or the second reagent or both the first reagent and the sample to the reaction vessel;
a sample dispensing mechanism disposed on a third track configured to aspirate the sample from the sample disk and dispense the sample to the reaction vessel positioned at a first dispensing position and to the reaction cell positioned at a second dispensing position;
a second reagent vessel disposed on the third track of the sample dispensing mechanism, the reaction vessel being provided on at least one of the second and third tracks; and
a control unit configured to control the first second reagent dispensing mechanisms and the sample dispensing mechanism, wherein
the control unit is configured to perform at least three processes including:
controlling the automatic analysis device to perform the analysis, according to a first process in which the analysis does not require both of the first and second reagents, by using the sample dispensing mechanism and the first reagent dispensing mechanism to dispense the sample and one of the first and second reagents;
controlling the automatic analysis device, according to a second process in which the analysis does require both of the first and second reagents and in which an incubation time is not required for the analysis, to dispense the sample and the first reagent, using the sample dispensing mechanism, to the reaction vessel positioned at the first dispensing position, dispense the second reagent to one of the reaction cells, and thereafter dispense the second reagent to the reaction vessel using the second reagent probe, and controlling the automatic analysis device, according to a third process in which the analysis does require both of the first and second reagents and in which the incubation time is required for the analysis, to dispense the sample, using the sample dispensing mechanism, to one of the reaction cells positioned at the second dispensing position, dispense the first reagent into the one the reaction cells containing the sample, dispense the second reagent to another reaction cell, and thereafter dispense the sample and first reagent from the one of the reaction cells to the reaction vessel, using the second reagent mechanism, and thereafter dispense the second reagent to the reaction vessel from the another reaction cell using the second reagent mechanism.

2. The automatic analysis device according to claim 1, wherein the reaction cell is disposed on a circumference of a reaction disk, the first dispensing position is disposed on the third track of the sample dispensing mechanism, the second dispensing position and a third dispensing position are disposed on a fourth track of the reaction disk, and at the third dispensing position, the sample dispensing mechanism aspirates a mixed solution in the reaction cell to which the sample and the first reagent are dispensed.

3. The automatic analysis device according to claim 2, wherein the second dispensing position and the third dispensing position are respectively disposed on intersections of the third track of the sample dispensing mechanism and the fourth track of the reaction disk.

4. The automatic analysis device according to claim 2, wherein in the case where the incubation is not required for the analysis, the first reagent is a diluted solution, and the diluted solution is dispensed from the second reagent vessel disposed adjacent to the reaction vessel at the first dispensing position.

5. The automatic analysis device according to claim 1, wherein when dispensing the sample and the first reagent to the reaction vessel, the sample and the first reagent are dispensed separately.

6. The automatic analysis device according to claim 1, wherein when dispensing the sample and the first reagent to the reaction vessel, a predetermined amount of the sample and the first reagent are aspirated continuously and dispensed to the reaction vessel simultaneously.

7. The automatic analysis device according to claim 5, wherein the sample is aspirated after the first reagent is aspirated.

8. The automatic analysis device according to claim 7, wherein aspiration is performed such that an air layer is provided between the aspirated first reagent and the sample.

9. The automatic analysis device according to claim 8, wherein after aspiration of the first reagent and the air layer, an outer wall portion at a tip of a probe of the sample dispensing mechanism is cleaned.

* * * * *